US010405984B2

(12) United States Patent
McMinn

(10) Patent No.: US 10,405,984 B2
(45) Date of Patent: Sep. 10, 2019

(54) FEMORAL STEM PROSTHESIS

(71) Applicant: Derek James Wallace McMinn, Stourbridge (GB)

(72) Inventor: Derek James Wallace McMinn, Stourbridge (GB)

( * ) Notice: Subject to any disclaimer, the term of this patent is extended or adjusted under 35 U.S.C. 154(b) by 65 days.

(21) Appl. No.: 15/170,022

(22) Filed: Jun. 1, 2016

(65) Prior Publication Data

US 2016/0361174 A1 Dec. 15, 2016

(30) Foreign Application Priority Data

Jun. 9, 2015 (GB) .................................. 1510012.6

(51) Int. Cl.
*A61F 2/38* (2006.01)
*A61F 2/36* (2006.01)
*A61F 2/30* (2006.01)

(52) U.S. Cl.
CPC .......... *A61F 2/3676* (2013.01); *A61F 2/3609* (2013.01); *A61F 2/3662* (2013.01); *A61F 2/3859* (2013.01); *A61F 2002/3054* (2013.01); *A61F 2002/30156* (2013.01); *A61F 2002/30158* (2013.01); *A61F 2002/30884* (2013.01); *A61F 2002/365* (2013.01); *A61F 2002/3678* (2013.01); *A61F 2230/0063* (2013.01)

(58) Field of Classification Search
CPC .... A61F 2/3662; A61F 2/3672; A61F 2/3676; A61F 2002/3678; A61F 2002/3688; A61F 2002/369; A61F 2/3859; A61F 2/367; A61F 2/3609
See application file for complete search history.

(56) References Cited

U.S. PATENT DOCUMENTS

| 3,793,650 A | * | 2/1974 | Ling | .................... | A61F 2/30724 |
| | | | | | 623/23.46 |
| 4,404,693 A | * | 9/1983 | Zweymuller | ......... | A61F 2/3662 |
| | | | | | 623/23.29 |
| 4,840,632 A | * | 6/1989 | Kampner | ........... | A61B 17/1666 |
| | | | | | 623/22.36 |
| 2012/0172996 A1 | | 7/2012 | Ries et al. | | |
| 2014/0343685 A1 | | 11/2014 | Ranawat et al. | | |

FOREIGN PATENT DOCUMENTS

| DE | 10036636 A1 | 3/2001 |
| FR | 2636837 A1 | 3/1990 |

OTHER PUBLICATIONS

Search and Examination Report issued in a related United Kingdom Application No. GB1510012.6 dated Dec. 8, 2015.

* cited by examiner

*Primary Examiner* — Christopher D. Prone
(74) *Attorney, Agent, or Firm* — Morgan, Lewis & Bockius LLP

(57) ABSTRACT

A femoral stem prosthesis features a proximal section and a distal section, both of which have a medial edge and a lateral edge. The proximal section is generally wider in a medio-lateral direction than the distal section. The proximal section and the distal section both taper inwardly in a medio-lateral direction such that an anterior-posterior thickness of the medial edge is greater than an anterior-posterior thickness of the lateral edge.

20 Claims, 14 Drawing Sheets

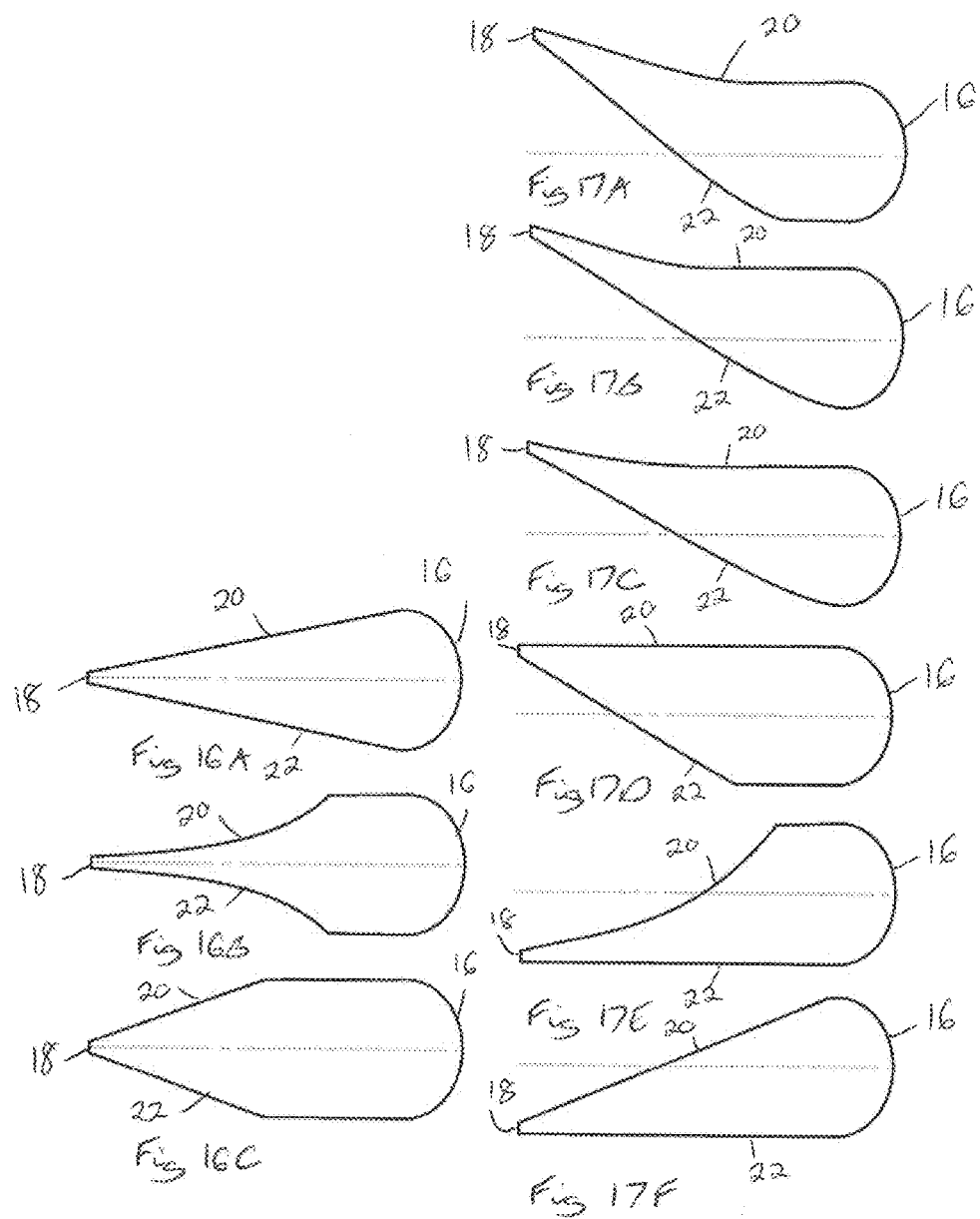

FEMORAL STEM PROSTHESIS

RELATED APPLICATION

This application claims priority to United Kingdom Patent Application No. 1510012.6, filed on Jun. 9, 2015, the entire disclosure of which is incorporated by reference herein.

FIELD OF THE INVENTION

The present invention relates to a femoral stem prosthesis. Particularly, but not exclusively, the invention relates to a femoral stem prosthesis for use in total hip replacement operations.

BACKGROUND TO THE INVENTION

Traditional total hip replacements involve inserting a stem of a femoral implant into the medullary canal of a patient's femur after the femur has been resected at the distal end of the femoral neck. The stem is usually tapered such that its sides gradually converge from a wider proximal end to a narrower distal end. This configuration allows the stem to fill the majority of the medullary canal as the femur gradually narrows in a distal direction and this helps to anchor the implant in the femur. A rounded tip is provided at the distal end of the stem and a femoral neck and head is provided at the proximal end. The femoral head is constituted by a spherical ball configured for location within a corresponding acetabular cup.

A femoral stem implant may be designed for cemented or uncemented use. In relation to uncemented stems there are two principal designs. The most common design comprises a flat tapered stem with parallel anterior and posterior surfaces. Previously, tubular stems were common but now tapered tubular stems are more common. All known designs have a porous proximal coating for bone in-growth and all work reasonably well.

Nearly all known stem designs have a medial curvature to match the medial curvature of the inside of the femur. However, nearly all designs ignore the curvature of the inside of the lateral wall of the femur and have a straight or angled lateral border instead.

US2012/0172996 discloses a stem design that includes a medial to lateral inward taper in a proximal section and a lateral to medial inward taper in a distal section. Accordingly, the taper direction changes along the length of the stem such that there are relatively large load bearing areas on the wide medial surface proximally and on the wide lateral surface distally. It is claimed that this helps to promote self-centering of the stem in the medullary canal so as to avoid varus or valgus mal-alignment. Notably, the stem is design to prevent rotation of the implant during and after insertion.

It is an aim of the present invention to provide an improved femoral stem prosthesis.

SUMMARY OF THE INVENTION

According to a first aspect of the present invention there is provided a femoral stem prosthesis comprising a proximal section and a distal section, both sections having a medial edge and a lateral edge; the proximal section being generally wider in a medio-lateral direction than the distal section; and wherein the proximal section and the distal section both taper inwardly in a medio-lateral direction such that an anterior-posterior thickness of the medial edge is greater than an anterior-posterior thickness of the lateral edge.

Thus, embodiments of the present invention provide a femoral stem with a medio-lateral inward taper along the entire length of the stem. This is unlike in US2012/0172996 where the distal section tapers outwardly in a medio-lateral direction. Furthermore, this feature of the present invention has the advantage that the natural version of the femur can be adjusted by the surgeon through rotation of the stem around an axis through the medial side. The stem therefore provides additional rotational correction for the position of the femoral head.

It will be understood that use of the terms medial edge and lateral edge, respectively, denote the boundary of the prosthesis on the medial and lateral sides. In other words, they relate to the nearest surfaces that are visible when viewing the prosthesis from either the medial or lateral sides.

A disadvantage of current non-modular stems is the relative inability to insert the stem in such a way as to alter the natural version of the femur. Many women have excessive anteversion of the upper femur and femoral neck and it would be desirable to decrease anteversion in these women with mild or moderate developmental dysplasia. Some men with slipped upper femoral epiphysis morphology have too little anteversion or even retroversion. In these patients it would be desirable to increase the anteversion. The present invention therefore provides a femoral stem prosthesis that can be used to correct or alter the natural version of the femur in such patients.

The feature that tends to limit the amount of anteversion possible with a femoral stem is a camels hump of cortical bone that protrudes into the postero-lateral corner of the femoral canal. This is a downwards extension of cortical bone from the piriformis fossa. However, in embodiments of the present invention, the medio-lateral inward taper of the stem allows the relatively thin lateral edge to miss the hump of cortical bone in the postero-lateral corner of the femoral canal, thereby allowing a greater range of version adjustment.

As is known in the art, the stem anteversion will be measured with reference to a tangent to the back of the distal femoral condyles.

An advantage of embodiments of the present invention is that a greater range of anteversion is permitted when compared with traditional stems due to the relatively thin nature of the lateral edge when compared to the medial edge. Natural anteversion of a femoral head is approximately 20 degrees. However, current stem implants only allow approximately 4 degrees of anteversion. This can cause the stem to tilt when under pressure in use such that the distal end of the stem will contact and push against the back of the femur. Understandably, this can be extremely painful and may require revision surgery.

The configuration of the present invention allows anteversion of up to approximately 11 degrees (7 degrees more than the prior art), which much more closely matches natural anteversion and helps to prevent forward tilting of the stem causing the distal end to bear against the posterior of the femur. Embodiments of the present invention are also less likely to dislocate as with more normal anteversion of the femoral stem the prosthetic neck is less likely to impinge against the anterior prosthetic cup edge and the prosthetic head is less likely to dislocate from the back of the prosthetic cup with flexion, internal rotation and adduction of the hip.

It should be noted that embodiments of the present invention may be suitable for use as uncemented stems as the large surface area provided by the wide proximal section (which can be considered as a 'sail') can help to aid fixation, resist rotation around a longitudinal axis through the medial side, lock the stem in position in the medullary canal and provide a large surface area for bone in-growth.

It will be understood that a comparison between the thickness of the medial edge when compared to the lateral edge is with reference to locations on the same transverse plane.

The anterior-posterior thickness of the lateral edge of the proximal section may be less than the anterior-posterior thickness of the lateral edge of the distal section.

The anterior-posterior thickness of the lateral edge of the proximal section may be 2, 3, 4, 5, 6, 7 or 8 mm. Similarly, the anterior-posterior thickness of the lateral edge of the distal section may be in the range of 5-15 mm.

The anterior-posterior thickness of the medial edge at the top of the proximal section may be selected from the following range: 9, 9.5, 10, 10.5, 11, 11.5, 12, 12.5, 13, 13.5, 14, 14.5, 15, 15.5, 16, 16.5, 17, 17.5, 18, 18.5, 19, 19.5 or 20 mm.

The stem may comprise a planar anterior and/or posterior surface. In a particular embodiment, the anterior and posterior surfaces may have a constant angle there-between. The angle may be in the range 15 to 45 degrees or 20 to 25 degrees. In some embodiments, the angle may be 22.5 degrees. It will be understood that the angle between the anterior and posterior surfaces will define the taper of the stem in the medio-lateral direction.

The stem may generally taper inwardly in a distal direction towards a distal tip. Thus, the anterior and posterior surfaces may taper inwardly in a distal direction. In addition, the medial edge of the proximal section may taper inwardly in a distal direction. Furthermore, the medial edge of the distal section may taper inwardly in a distal direction.

The lateral edge of the proximal and distal sections may also taper inwardly in a distal direction.

A shoulder may be formed where the lateral edge of the proximal section meets the lateral edge of the distal section. The shoulder may help to provide rotational stability (e.g. in a medio-lateral plane). It may also serve to lock the stem in position in the medullary canal, particularly during uncemented use.

In some embodiments, the lateral edge of the proximal section is narrower than the lateral edge of the distal section.

The medial edge may have a transverse cross-section that is curved, rounded, oval, square, trapezoidal or otherwise shaped. In particular embodiments, the medial edge may have a transverse cross-section that is semi-circular. This is advantageous in that a longitudinal axis through a centre of a radius of curvature forming the medial edge may serve as a rotational axis for adjustment of the version of the stem in the femur.

The lateral edge may have a transverse cross-section that is curved, rounded, oval, square, trapezoidal or otherwise shaped. In particular embodiments, the lateral edge may have a transverse cross-section that is generally flat or gently curved in an anterior-posterior direction.

The lateral edge of the distal section may comprise a proximal to distal curve. This has the advantage that the stem will more closely match the curved lateral wall of a normal femur (e.g. when compared to known planar or cylindrical tapered stems). It will therefore have better load bearing capabilities.

The distal section may comprise a flattened tapered tubular structure (i.e. with curved medial and lateral edges and planar anterior and posterior surfaces). In which case, the shape of the lateral edge may mirror the shape of the medial edge although the presence of the medio-lateral taper will mean that the thickness of the lateral edge is less than the thickness of the medial edge until the tip is reached.

The stem may further comprise a neck for a femoral head. The neck may be configured in accordance with the applicant's published EP2616011 such that an offset sleeve and/or femoral head (i.e. having an axis of rotation of an inter-engaging element being parallel to but offset from a central axis of the component) can be located on the neck in a number of different orientations to further alter the version angle. For example, the neck may comprise anti-rotational elements in the form of recessed mating surfaces for engagement with complementary surfaces in the offset sleeve/head. It is believed that embodiments of the present invention could be used in conjunction with an offset sleeve or head to provide up to a further 10 degrees of version, therefore providing in combination a total version adjustment range of approximately 20 degrees.

One or more portions of the stem may be configured to be cemented to the femur, in use, or they may be configured such that bone in-growth will fix the stem in place. Thus, one or more portions of the stem may comprise a porous surface. The porous surface may be provided by a porous coating, for example, by providing (cast or sintered) beads or bead portions on the surface or by plasma spraying material such as titanium onto the surface. In some embodiments, the porous surface may be constituted by a porous lattice (for example, as described in the Applicant's published EP2515958).

The femoral stem prosthesis may be formed of material comprising cobalt chrome or any other bio-acceptable material such as titanium, stainless steel, zirconium alloy, polymer, polymer composite such as epoxy resin—carbon fibre composite or ceramic.

According to a second aspect of the present invention there is provided a femoral implant comprising the femoral stem prosthesis according to the first aspect of the invention plus a femoral head.

The femoral head of the implant may comprise a part-spherical external surface configured to be received within a corresponding acetabular cup.

The femoral head of the implant may be integral with the stem or may be separable therefrom. Where the femoral head is separable from the stem, both the femoral head and the stem may comprise respective inter-fitting parts. In one embodiment, a frustoconical neck may extend from the proximal end of the stem to be received in a complementary shaped cavity in the internal portion of the femoral head, prior to insertion of the implant into a patient. The neck may be configured for a tight frictional fit in the cavity (for example, by including a so-called Morse taper) and/or may be cemented or glued therein.

In some embodiments, the implant may comprise a sleeve configured for location between the neck and the head.

According to a third aspect of the present invention there is provided a hip joint prosthesis comprising the femoral implant according to the second aspect of the present invention and an acetabular cup configured to receive the femoral head of said femoral implant.

The optional features described above in relation to the first aspect of the present invention may also be applied to the second and third aspects of the invention, where applicable.

BRIEF DESCRIPTION OF THE DRAWINGS

By way of example only, specific embodiments of the present invention are described in more detail below with reference to the accompanying drawings, in which:

FIGS. 16A-C show cross-sectional views similar to that shown in FIG. 7 but showing optional universal variants comprising different forms of medio-lateral tapers in accordance with embodiments of the invention;

FIGS. 17A-F show cross-sectional views similar to those shown in FIGS. 16A-C but showing optional variants that are either left or right-handed and which, again, comprise different forms of medio-lateral tapers in accordance with embodiments of the invention;

DETAILED DESCRIPTION OF CERTAIN EMBODIMENTS

Figure 1:
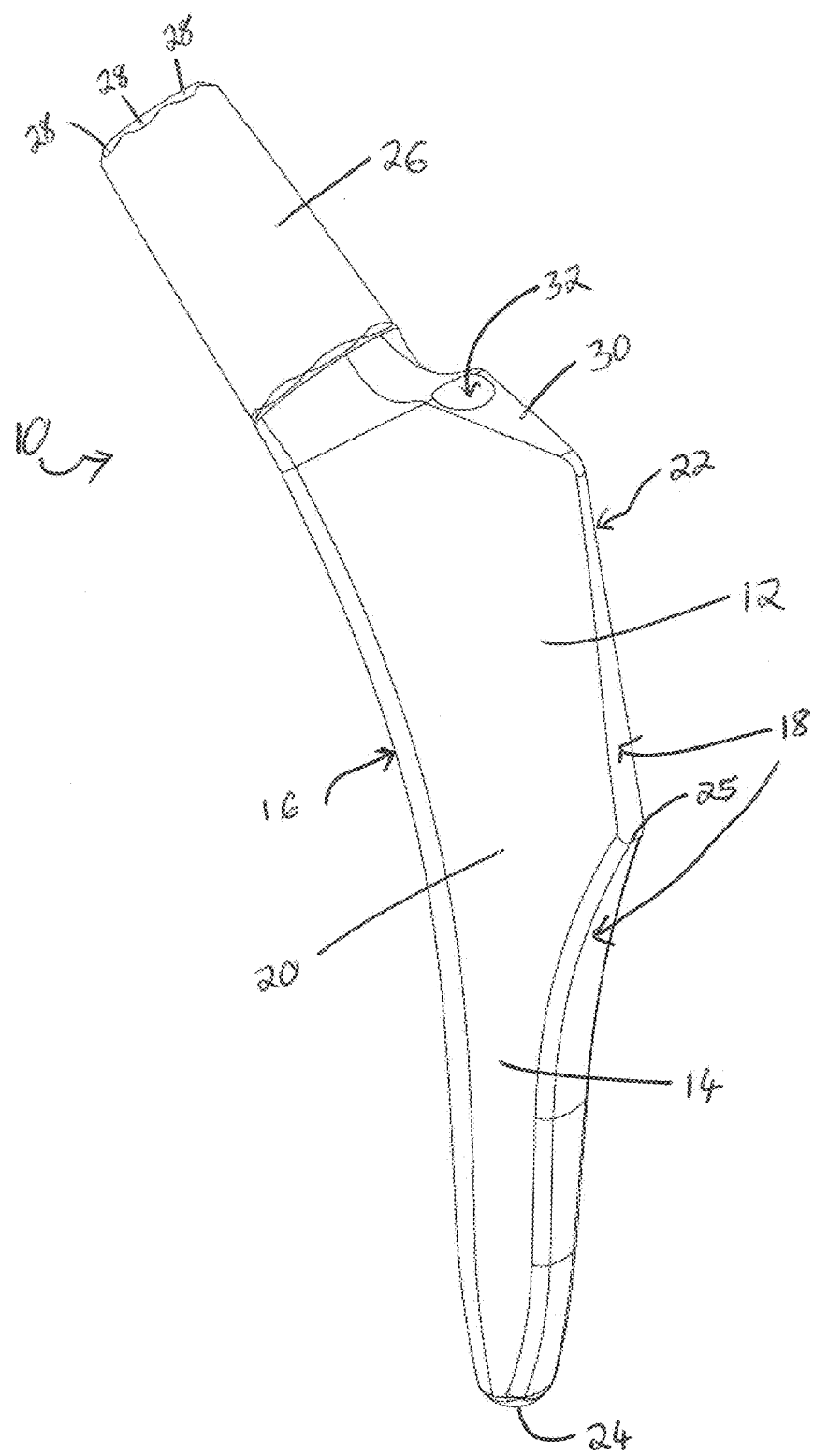
FIG. 1 shows a lateral isometric view of a femoral stem prosthesis in accordance with a first embodiment of the present invention.

With reference to FIGS. 1 through 13B, there is illustrated a femoral stem prosthesis 10 according to a first embodiment of the present invention. The femoral stem prosthesis 10 comprises a proximal section 12 and a distal section 14. Each section has a medial edge 16 and a lateral edge 18. The proximal section 12 is generally wider in a medio-lateral direction than the distal section 14. Furthermore, the proximal section 12 and the distal section 14 both taper inwardly in a medio-lateral direction such that an anterior-posterior thickness of the medial edge 16 is greater than an anterior-posterior thickness of the lateral edge 18.

As shown in FIG. 1, the anterior-posterior thickness of the lateral edge 18 of the proximal section 12 is less than the anterior-posterior thickness of the lateral edge 18 of the distal section 14. In this particular embodiment, the anterior-posterior thickness of the lateral edge 18 of the proximal section 12 tapers inwardly in a distal direction from approximately 5 mm to approximately 2 mm. Similarly, the anterior-posterior thickness of the lateral edge 18 of the distal section 14 is in the range of 10-5 mm. In the current embodiment, the anterior-posterior thickness of the medial edge 18 at the top of the proximal section 12 is 12 mm.

It should be noted that, although in some of the Figures (e.g. FIGS. 1, 5, 10 and 13A-B) it may appear as though the lateral edge 18 of the proximal section 12 expands outwardly in a distal direction, in fact the opposite is the case, and the lateral edge 18 tapers inwardly in a distal direction. However, due to the fact that the bottom of the lateral edge 18 of the proximal section 12 is located further forwards in a lateral direction it appears larger than the top of the lateral edge 18 that is located further away from the viewer. In all embodiments shown, the anterior to posterior thickness of the stem 10 constantly tapers inwardly in a distal direction.

Figure 9:
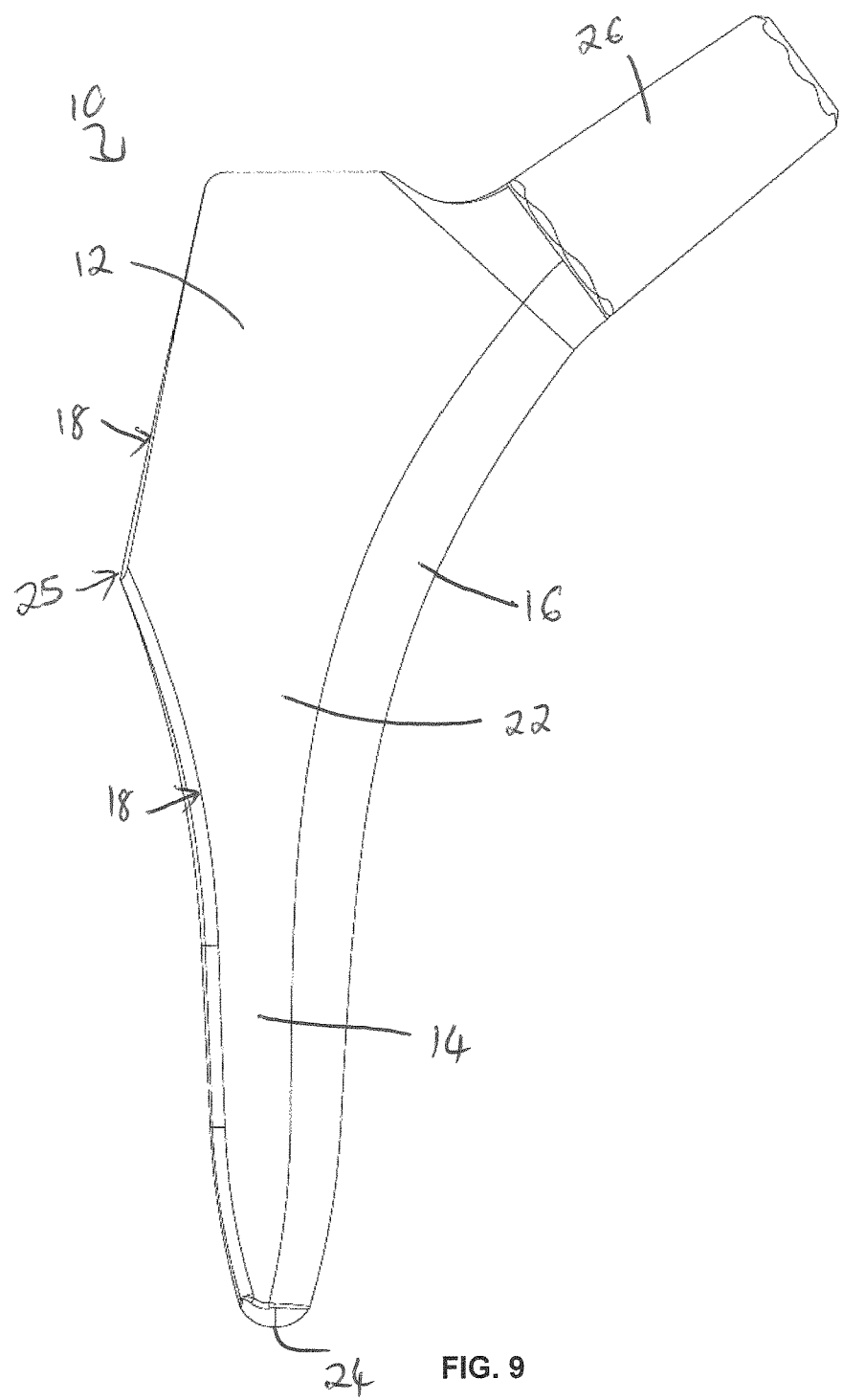
FIG. 9 shows a posterior to anterior view of the stem of FIG. 1.

The stem 10 comprises a planar anterior surface 20 and a planar posterior surface 22 (shown in FIG. 9). The stem 10 generally tapers inwardly in a distal direction towards a distal tip 24.

A shoulder 25 is formed where the lateral edge 18 of the proximal section 12 meets the lateral edge 18 of the distal section 14.

Figure 13A:
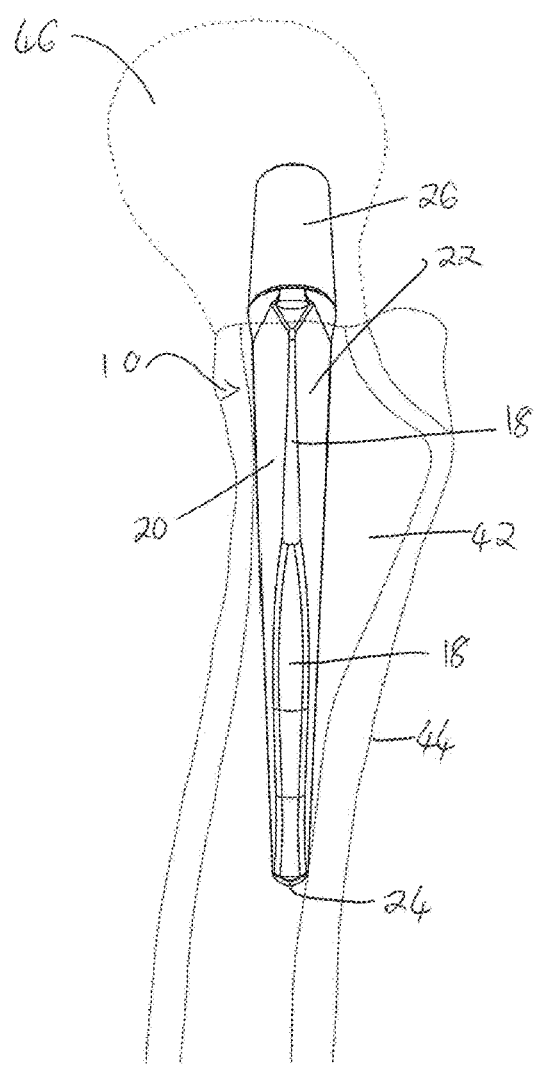
FIG. 13A shows a lateral to medial schematic view of the stem of FIG. 1 when inserted into the medullary canal of a femur, in a first position.
Figure 13B:
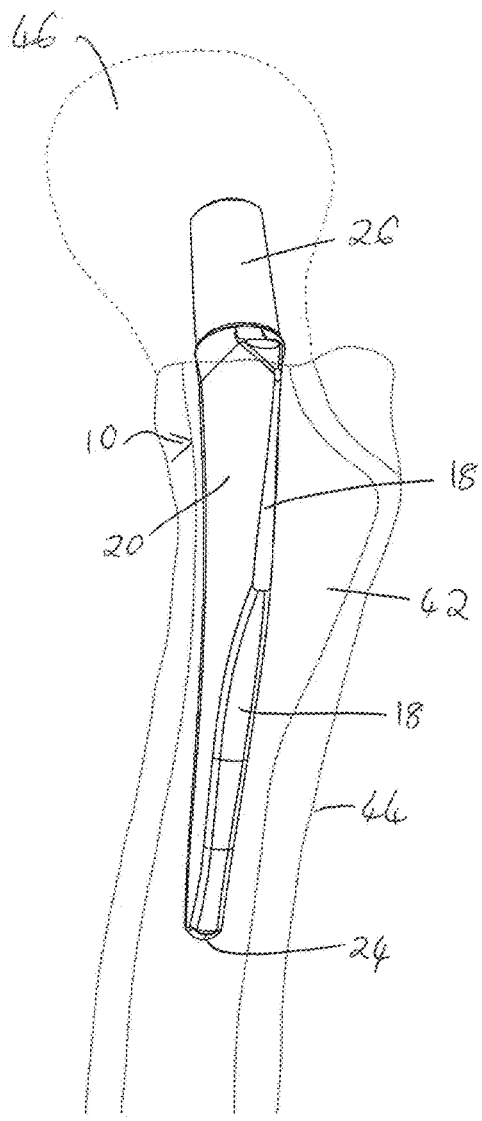
FIG. 13B shows a view similar to FIG. 13A but when the stem is inserted into the medullary canal of the femur, in a second position.

A neck 26 is provided at a proximal end of the stem 10 for attachment to a femoral head (e.g. as illustrated in FIGS. 13A and 13B). The neck 26 has a longitudinal axis that is at an angle β of approximately 37 degrees with respect to a transverse plane through the stem 10.

Figure 8:
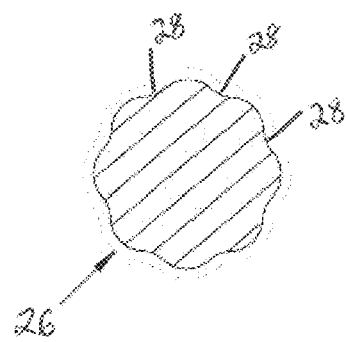
FIG. 8 shows the cross-sectional view taken along line GG in FIG. 2.

As shown in FIG. 8, the neck 26 is configured in accordance with the applicant's published EP2616011 such that an offset sleeve and/or femoral head (i.e. having an axis of rotation of an inter-engaging element being parallel to but offset from a central axis of the component) can be located on the neck 26 in a number of different orientations to further alter the version angle. More specifically, the neck 26 comprises anti-rotational elements in the form of recessed mating surfaces or channels 28 for engagement with complementary surfaces in the offset sleeve/head. It is therefore believed that embodiments of the present invention could be used in conjunction with an offset sleeve or head to provide up to a further 10 degrees of version, therefore providing in combination a total version adjustment range of approximately 20 degrees. It should be noted that, for clarity reasons, the whole extent of the channels 28 along the length of the neck 26 are not shown in the remaining Figures.

The proximal section 12 has a top surface 30 which includes a circular recess 32 for receipt of an instrument to aid insertion of the stem 10 into the medullary canal of a patient's femur.

Figure 2:
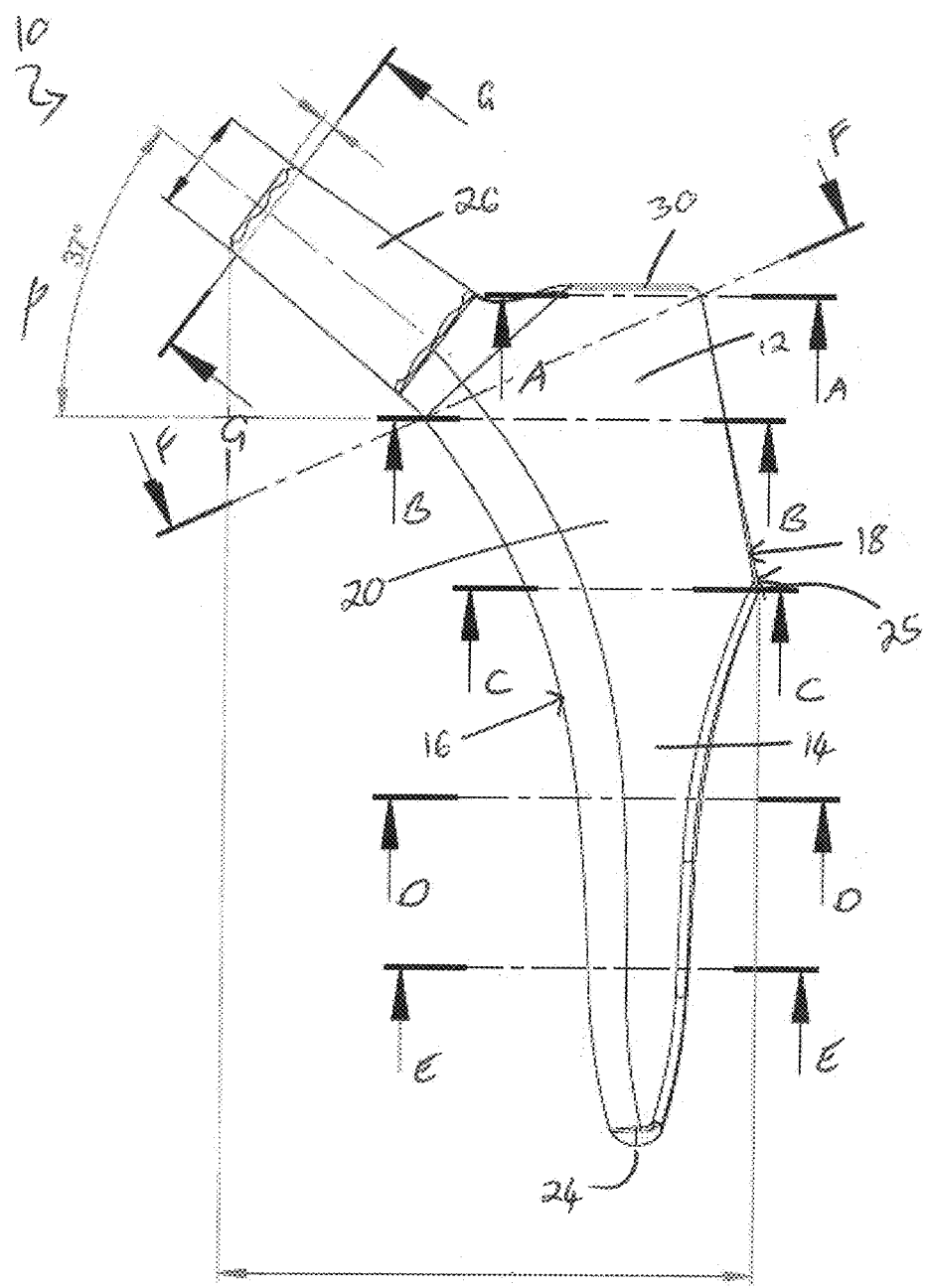
FIG. 2 shows an anterior to posterior view of the stem of FIG. 1 indicating the planes for various cross-sectional views detailed below.

As best shown in FIG. 2, the lateral edge 18 of the distal section 14 comprises a proximal to distal curve. This has the advantage that the stem 10 will more closely match the curved lateral wall of a normal femur (e.g. when compared to known planar or cylindrical tapered stems). It will therefore have better load bearing capabilities. The medial edge 16 also comprises a proximal to distal curve to match the curved medial wall of the femur.

As shown in FIGS. 3A to 3E, the anterior and posterior surfaces 20, 22 have a constant angle α there-between of 22.5 degrees, defining the medio-lateral taper of the stem 10, which is constant along the entire length of the stem 10.

As also shown in FIGS. 3A to 3E, the medial edge has a transverse cross-section that is semi-circular (although it could be a different shape in other embodiments). Furthermore, the lateral edge 18 has a transverse cross-section that is generally flat or gently curved in an anterior-posterior direction.

Figure 3A:
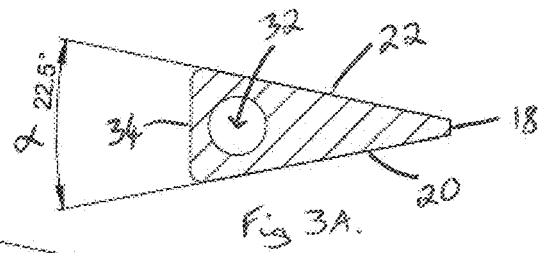
FIGS. 3A-3E show the cross-sectional views taken along lines AA, BB, CC, DD and EE in FIG. 2, respectively.
Figure 3B:
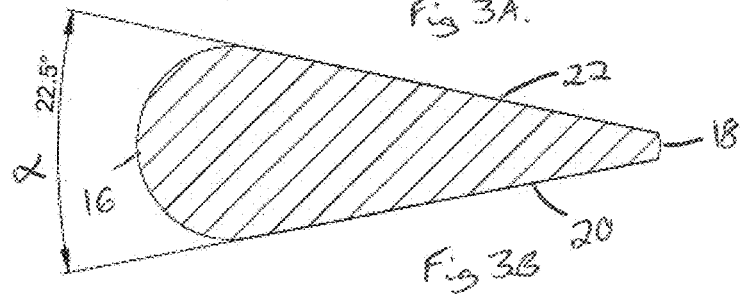
Figure 3C:
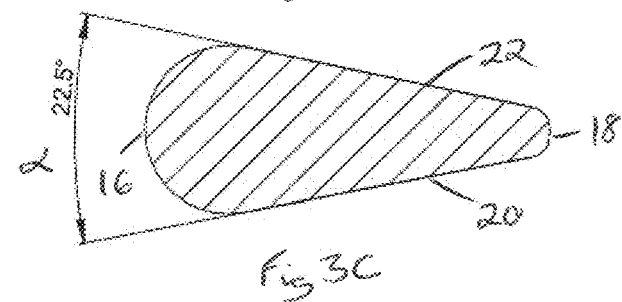
Figure 3D:
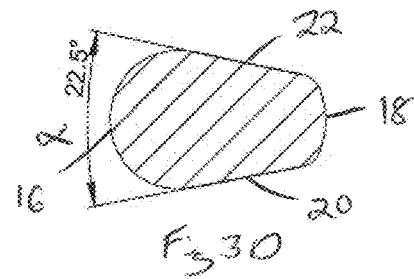
Figure 3E:
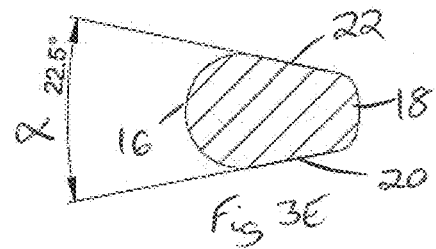

It should be noted that FIG. 3A terminates medially at a straight surface 34 which forms a small shoulder leading into the neck 26. As such, surface 34 is not part of the medial edge 16 as per FIGS. 3B to 3E.

Figure 4:
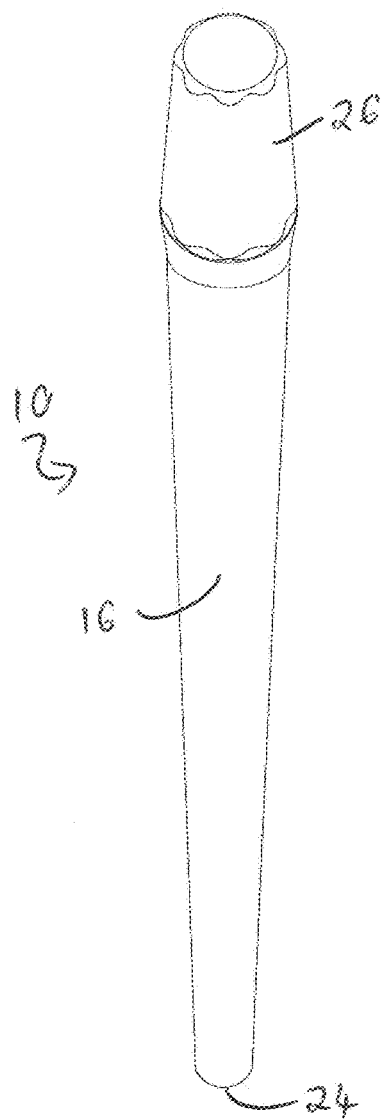
FIG. 4 shows a medial to lateral view of the stem of FIG. 1.
Figure 5:
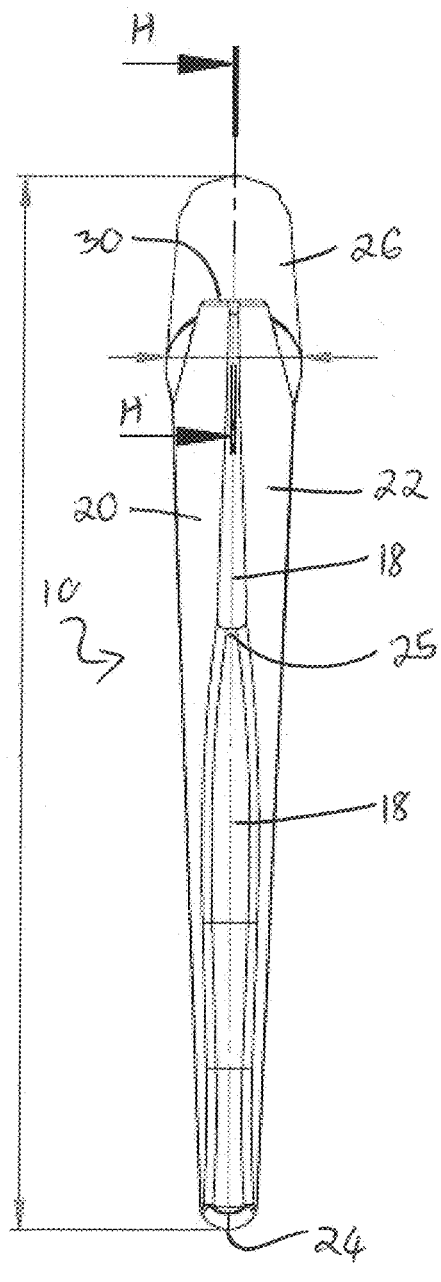
FIG. 5 shows a lateral to medial view of the stem of FIG. 1 indicating a plane for the cross-sectional view of FIG. 6.

FIGS. 4 and 5 show, respectively, the stem 10 from a medial and a lateral side. Accordingly the thin nature of the lateral edge 18 is particularly evident.

Figure 6:
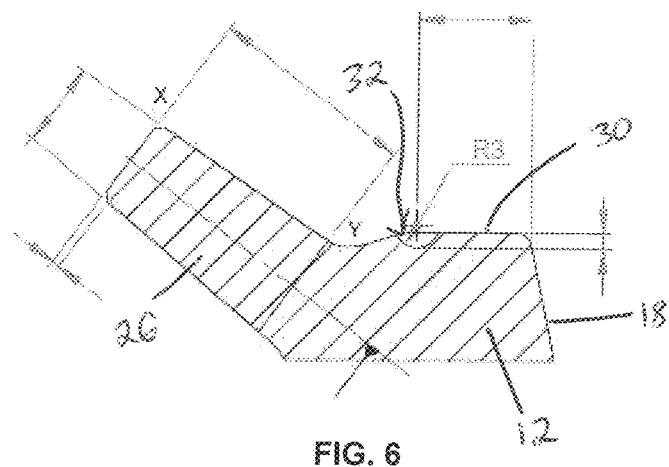
FIG. 6 shows the cross-sectional view taken along line HH in FIG. 5.

FIG. 6 shows a cross-section taken along line HH in FIG. 5 and shows the curved nature of the recess 32 in the top surface 30 of the proximal section 12.

Figure 7:
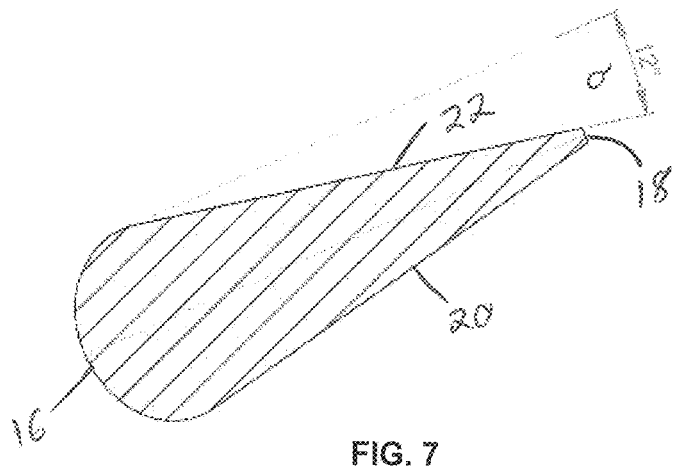
FIG. 7 shows the cross-sectional view taken along line FF in FIG. 2.
Figure 12:
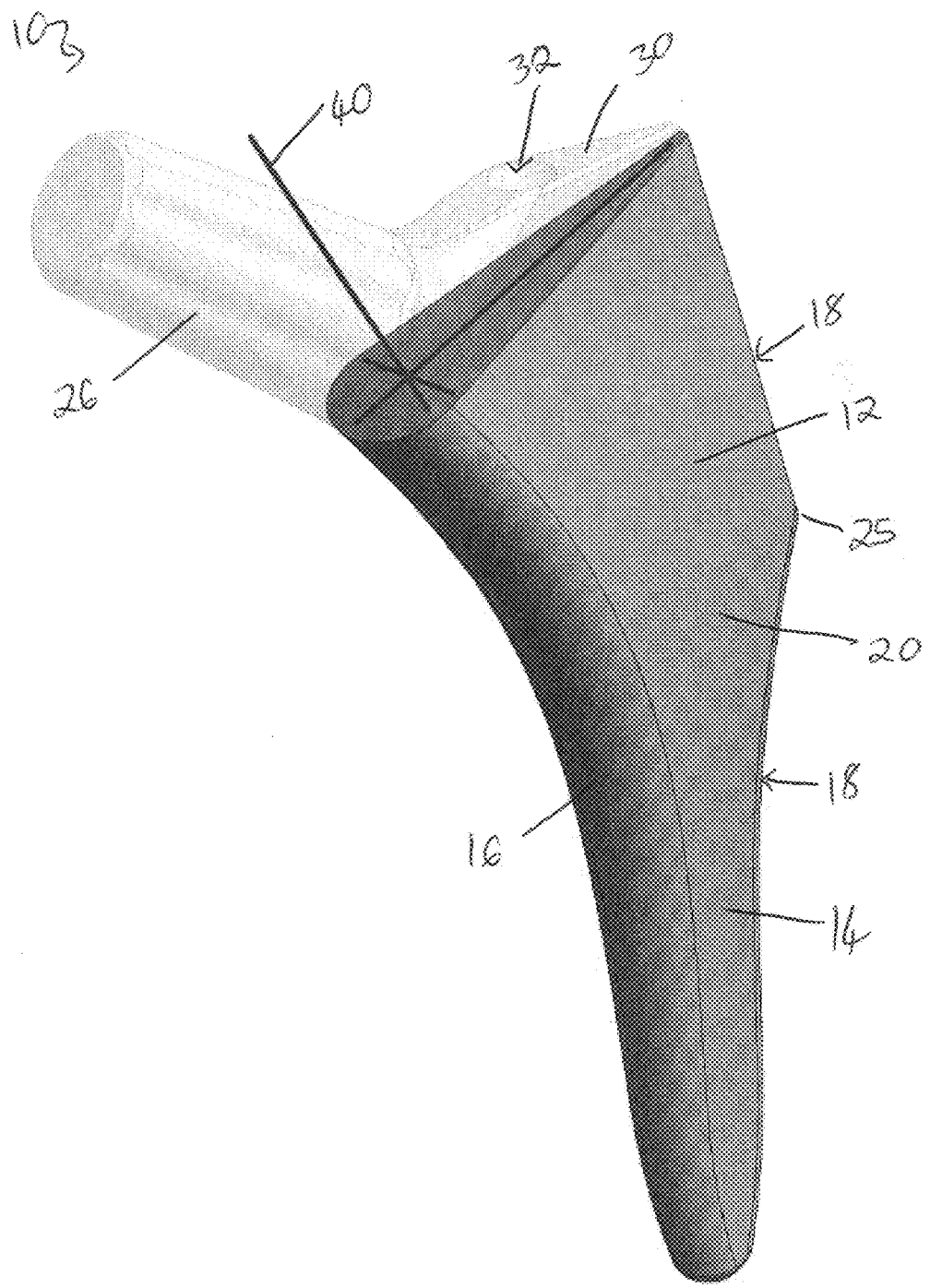
FIG. 12 shows a medial isometric view of the stem of FIG. 1 indicating an axis for rotation of the stem.

FIG. 7 shows the cross-sectional view taken along line FF in FIG. 2. This plane is normal to the axis of rotation of the stem 10 which is shown in FIG. 12 and which passes through the centre of the radius of curvature of the medial edge 16. As illustrated in FIG. 7, the medio-lateral taper is at an angle α of 12 degrees when compared to traditional parallel-sided stems.

As described above, FIG. 8 shows the cross-sectional view taken along line GG in FIG. 2 and shows the recessed surfaces 28 configured to mate with corresponding surfaces on an offset sleeve or head prosthesis to allow further adjustment of the version. Alternatively, stems according to embodiments of the present invention can be used with standard sleeves and heads were no further adjustment is required.

Figure 10:
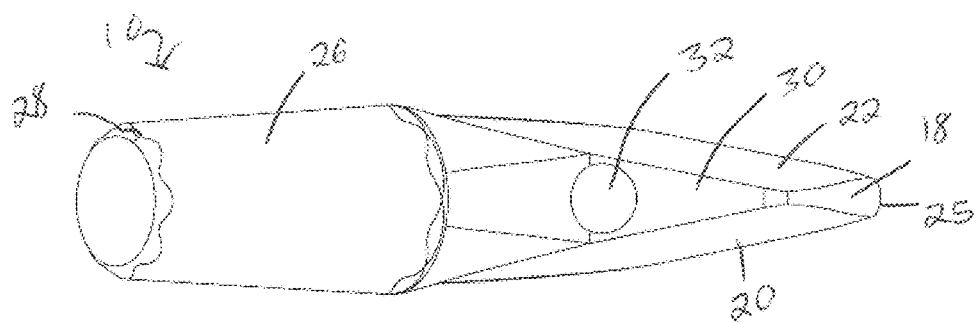
FIG. 10 shows a superior view of the stem of FIG. 1.
Figure 11:
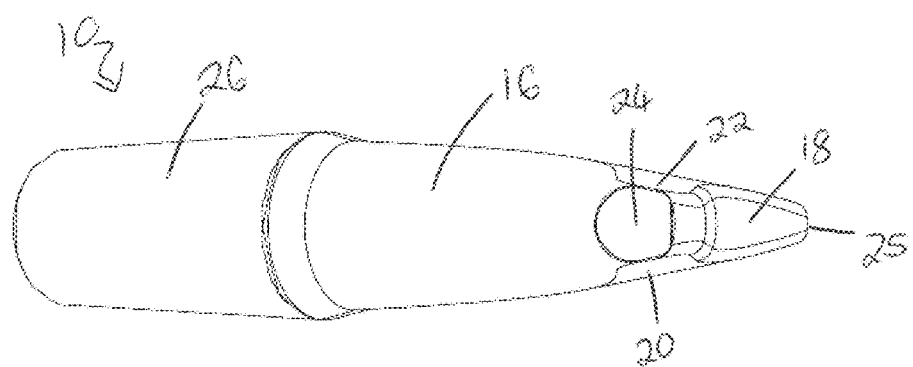
FIG. 11 shows an inferior view of the stem of FIG. 1.

FIG. 9 shows the posterior surface of the stem of FIG. 1 and FIGS. 10 and 11, respectively, show superior and inferior views of the stem 10.

FIG. 12 shows the rotation axis 40 of the stem 10 which is constituted by a longitudinal axis through a centre of a radius of curvature forming the medial edge 16 of the stem 10. By rotating the stem 10 about the axis 40, the version of the neck 26 can be adjusted so that the surgeon can insert the stem 10 with a desired degree of version to correct for femoral abnormalities.

FIGS. 13A and 13B show a lateral to medial schematic view of the stem 10 of FIG. 1 when inserted into the medullary canal 42 of a femur 44, in a first and second position, respectively. In the first position shown in FIG. 13A, the tip 24 of the stem 10 is in contact with the posterior wall of the femur and may press against this when load is applied through the femoral head 46, which may cause pain or discomfort. In the second position shown in FIG. 13B, the stem 10, has been rotated around the medial edge 16 and this has caused the lateral edge 18 to be located closer toward the posterior of the femur which, in turn, has repositioned the tip 24 in the centre of the medullary canal 42. Accordingly, embodiments of the present invention can improve the alignment of the stem 10 in the femur when viewed in the lateral profile. In addition, embodiments of the present invention can more closely reproduce the anteversion of a native femoral neck.

Figures 14A, 14B:
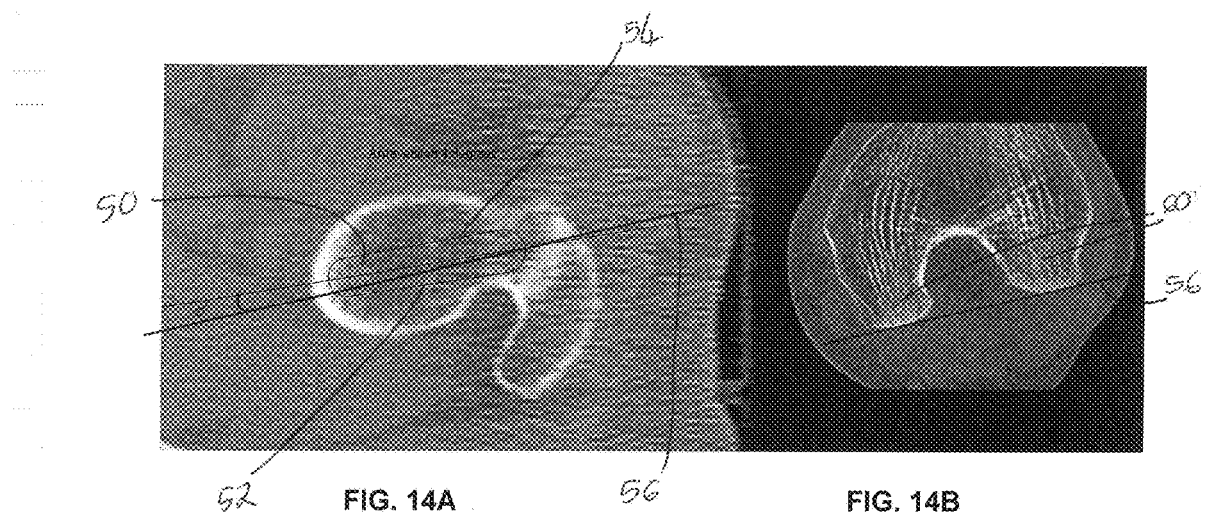
FIGS. 14A and 14B show, respectively, computerised tomography (CT) scans of a patient indicating the range of anteversion permitted using a traditional stem (comprising parallel anterior and posterior surfaces) with reference to a tangent to the rear of the femoral condyles.
Figures 15A, 15B:
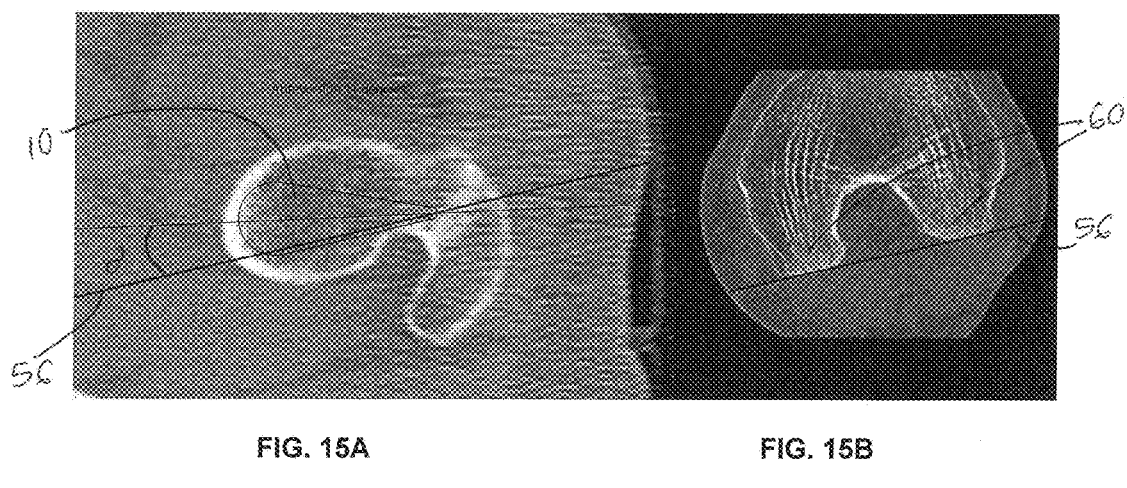
FIGS. 15A and 15B show, respectively, computerised tomography (CT) scans of a patient indicating the range of anteversion permitted using the stem of FIG. 1 (comprising tapering anterior and posterior surfaces) with reference to a tangent to the rear of the femoral condyles.

FIGS. 14A-B and 15A-B show, respectively, CT scans of a patient indicating the range of anteversion a permitted using a traditional flat taper stem 50 (comprising parallel anterior 52 and posterior 54 surfaces) when compared with present stem 10, with reference to a tangent 56 to the rear of the femoral condyles 60. FIGS. 14A and 14B show a slice through the neck resection level for total hip replacement, which corresponds to the stem section shown in FIG. 7. With tradition stem 50, the maximum anteversion a possible is 4 degrees. However, with the present stem 10 up to 12 degrees of anteversion may be possible. To achieve natural anteversion of 20 degrees, an offset sleeve or head could be used as described above to provide a further 8 degrees of anteversion.

FIGS. 16A-C show cross-sectional views similar to that shown in FIG. 7 but showing optional universal, symmetrical, variants comprising different forms of medio-lateral tapers in accordance with embodiments of the invention. More specifically, FIG. 16A corresponds to FIG. 7 and shows a straight medio-lateral taper from the curved medial edge 16 to the flat lateral edge 18. FIG. 16B shows a variant whereby a medial side of stem comprises parallel anterior 20 and posterior 22 surfaces which then curve inwardly at a lateral side of the stem toward the lateral edge 18. FIG. 16C shows a variant whereby a medial side of stem comprises parallel anterior 20 and posterior 22 surfaces which then taper straight inwardly at a lateral side of the stem toward the lateral edge 18. In each case, the stem is considered to comprise a medio-lateral taper even if, in some case, the taper is not provided over the entire cross-sections shown.

FIGS. 17A-F show cross-sectional views similar to those shown in FIGS. 16A-C but showing optional variants that are either left or right-handed and which, again, comprise different forms of medio-lateral tapers in accordance with embodiments of the invention. More specifically, FIG. 17A shows a variant that has a medial side similar to that of FIG. 16C but where the lateral side is shifted anteriorly such that the tapered portion is longer on the posterior side 22 than the anterior side 20. FIG. 17B shows a variant that is similar to that of FIG. 17A but wherein the posterior side tapers directly from the medial edge 16 to the lateral edge 18. FIG. 17C shows a variant that is similar to that of FIG. 17B but wherein the lateral edge 18 is not shifted so far anteriorly. FIG. 17D shows a variant that is similar to that of FIG. 17A but wherein the anterior surface 20 is parallel all the way to the lateral edge 18 such that only the posterior surface 22 forms a straight taper on the lateral side of the stem. FIG. 17B shows a variant that is similar to that of FIG. 17D but wherein the posterior surface 22 is parallel all the way to the lateral edge 18 such that only the anterior surface 22 forms a curved taper on the lateral side of the stem. FIG. 17F shows a variant that is similar to that of FIG. 17E but wherein the anterior surface 20 forms a straight taper from the medial edge 16 to the lateral edge 18.

An advantage of one-sided stems such as those shown in FIGS. 17A-F is that the amount of correction of anteversion can be greater than for symmetrical stems such as those of FIGS. 16A-C. However, a disadvantage is a doubling of instruments and implant inventory than one-sided stems would require.

Figure 18:
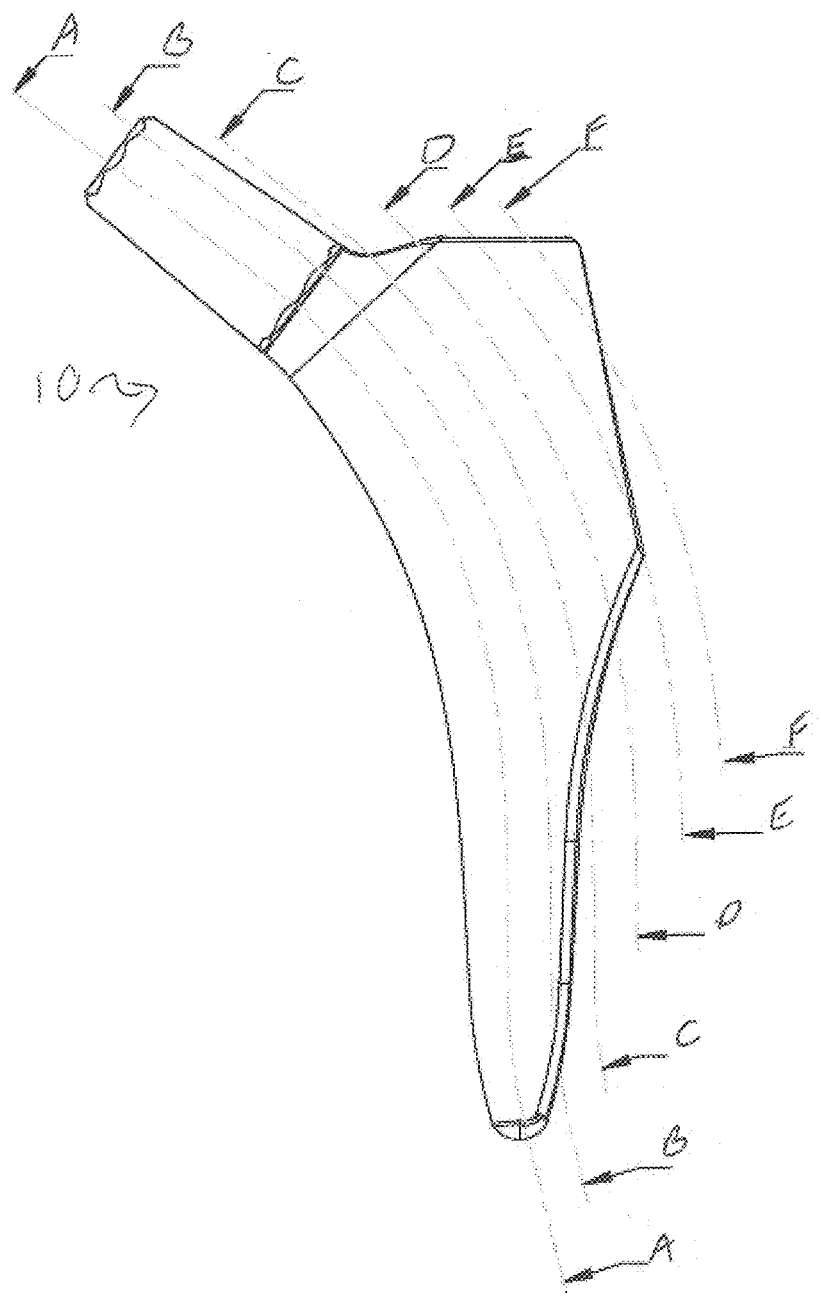
FIG. 18 shows a view similar to that of FIG. 2 but wherein a series of longitudinal cross-sections are illustrated, each of which is parallel to the medial curvature of the stem.
Figure 19:
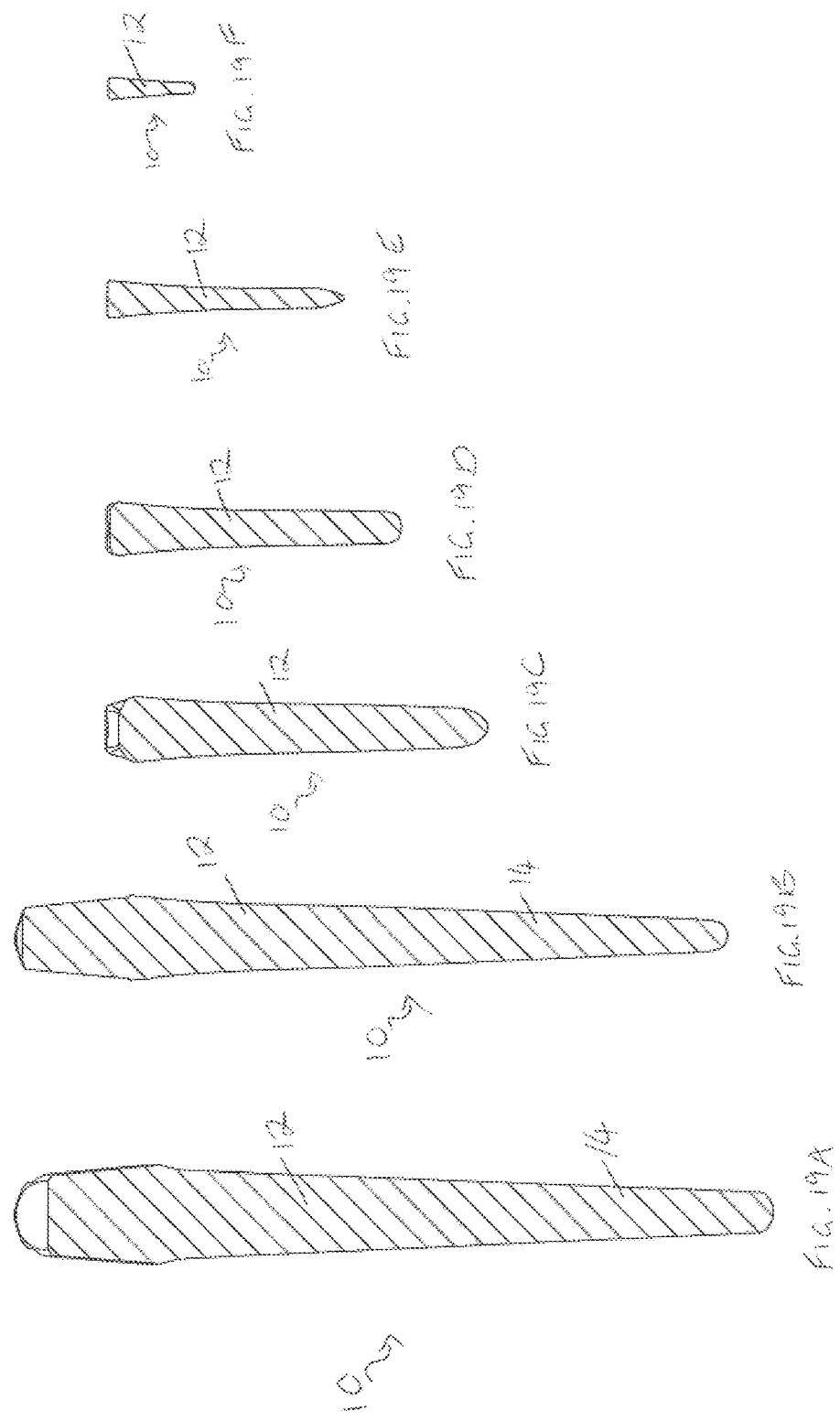
FIGS. 19A-F show the cross-sectional views taken along lines AA, BB, CC, DD, EE and FF in FIG. 18, respectively.

FIG. 18 shows a view similar to that of FIG. 2 but wherein a series of longitudinal cross-sections are illustrated, each of which is parallel to the medial curvature of the stem 10. As shown in each of the cross-sectional views of FIGS. 19A-F the stem 10 tapers inwardly in a distal direction across the entire length of the stem 10 from the proximal section 12 to the distal section 14.

Figure 20:
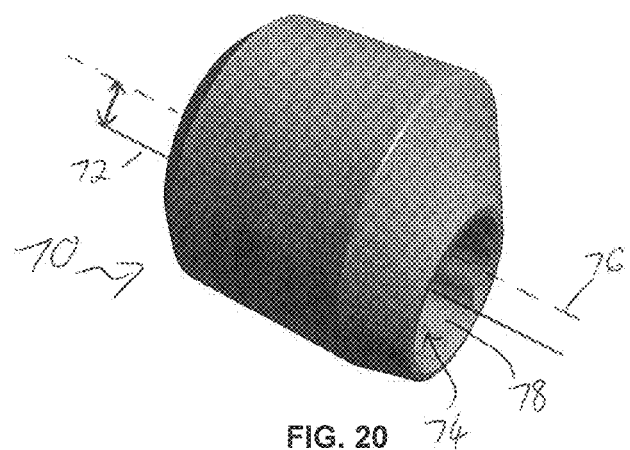
FIG. 20 shows an example of an offset sleeve for use with embodiments of the present invention.

FIG. 20 shows an example of an offset sleeve 70 for use with embodiments of the present invention. The sleeve 70 is configured in accordance with the applicant's published EP2616011 such an axis of rotation 72 of an inter-engaging recess 74 is parallel to but offset by approximately 5 mm from a central axis 76 of the sleeve 70 so that it can be located on the neck 26 of the femoral stem 10 in a number of different orientations to further alter the version angle. As explained in relation to FIG. 8, the neck 26 of the stem 10 includes channels 28 for engagement with complementary surfaces 78 in the recess 74 of the offset sleeve 70.

Figures 21A, 21B:
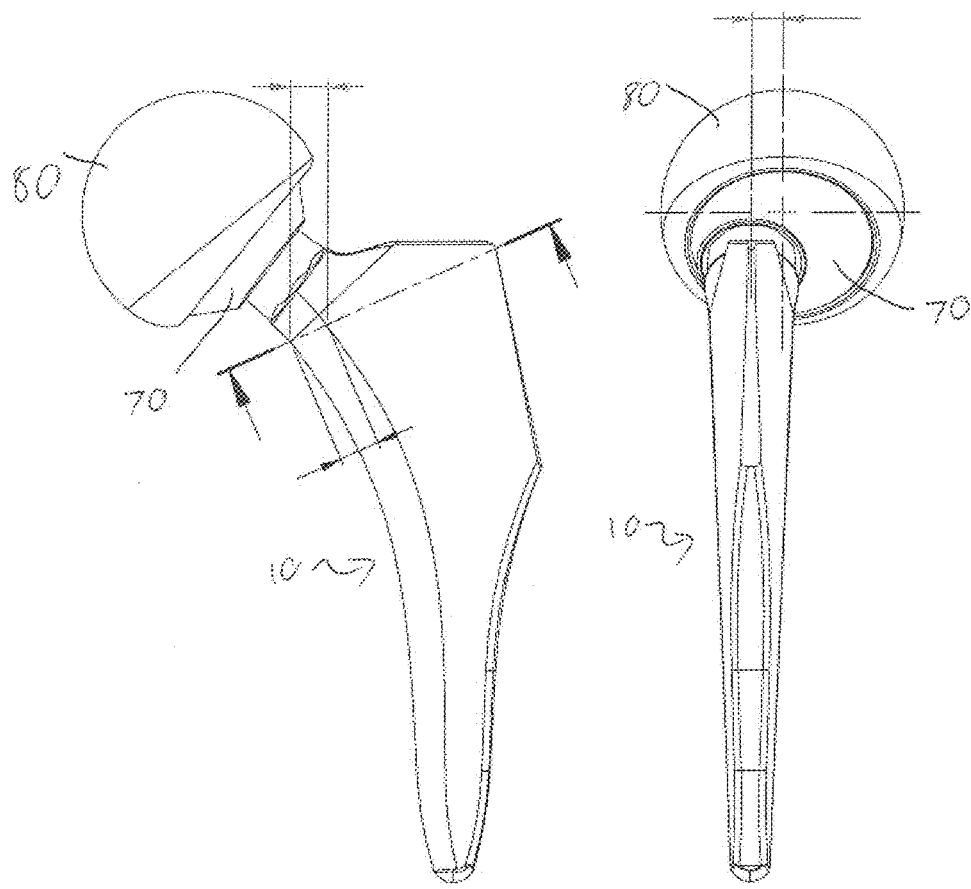
FIGS. 21A and 21B show a stem according to the first embodiment of the invention fitted with the offset sleeve and a femoral head prosthesis in both an anterior to posterior view and a lateral to medial view.

FIGS. 21A and B show the stem 10 fitted with the offset sleeve 70 and a femoral head prosthesis 80 in one configuration. As explained previously, by rotating the sleeve 70 with respect to the stem 10, a greater amount of anteversion can be achieved.

It will be understood that embodiments of the present invention variously provide for an improved femoral stem prosthesis 10 which can be used to correct version abnormalities. In addition, aspects of the present invention provide for an improved fixing of the implant in the femur, improved alignment of the stem within the medullary canal and a reduced risk of dislocation and stem rotation during use.

It will be appreciated by persons skilled in the art that various modifications may be made to the above embodiments without departing from the scope of the present invention as defined by the claims.

The invention claimed is:

1. A femoral stem prosthesis comprising:
a proximal section having a proximal medial edge and a proximal lateral edge and a distal section having a distal medial edge and a distal lateral edge, the distal medial edge and the distal lateral edge extending to a distal tip;
the proximal section being wider in a medio-lateral direction than the distal section; and
wherein the proximal section and the distal section both taper inwardly in a medio-lateral direction to form a medio-lateral inward taper along an entire length of the stem such that an anterior-posterior thickness of the proximal medial edge is greater than an anterior-posterior thickness of the proximal lateral edge and an anterior-posterior thickness of the distal medial edge is greater than an anterior-posterior thickness of the distal lateral edge along the entire length of the stem.

2. The femoral stem prosthesis according to claim 1 wherein the anterior-posterior thickness of the proximal lateral edge is less than the anterior-posterior thickness of the distal lateral edge.

3. The femoral stem prosthesis according claim 1 wherein the anterior-posterior thickness of the proximal lateral edge is 2, 3, 4, 5, 6, 7 or 8 mm.

4. The femoral stem prosthesis according to claim 1 wherein the anterior-posterior thickness of the distal lateral edge is in the range of 5-15 mm.

5. The femoral stem prosthesis according to claim 1 wherein the anterior-posterior thickness of the proximal medial edge at a top portion of the proximal section is selected from the following list: 9, 9.5, 10, 10.5, 11, 11.5, 12, 12.5, 13, 13.5, 14, 14.5, 15, 15.5, 16, 16.5, 17, 17.5, 18, 18.5, 19, 19.5 or 20 mm.

6. The femoral stem prosthesis according to claim 1 comprising a planar anterior and/or posterior surface.

7. The femoral stem prosthesis according claim 6 wherein the anterior and posterior surfaces have a constant angle there-between.

8. The femoral stem prosthesis according to claim 7 wherein the angle is in the range 15 to 45 degrees.

9. The femoral stem prosthesis according to claim 8 wherein the angle is 22.5 degrees.

10. The femoral stem prosthesis according to claim 7 wherein the angle is in the range 20 to 25 degrees.

11. The femoral stem prosthesis according to claim 1 wherein the proximal lateral edge has a top portion which tapers inwardly in a distal direction and a bottom portion which tapers outwardly in the distal direction.

12. The femoral stem prosthesis according to claim 1 wherein a shoulder is formed where the proximal lateral edge meets the distal lateral edge.

13. The femoral stem prosthesis according to claim 1 wherein the proximal lateral edge is narrower than the distal lateral edge.

14. The femoral stem prosthesis according to claim 1 wherein the proximal medial edge and/or the distal medial edge has a transverse cross-section that is curved, rounded, oval, square, or trapezoidal.

15. The femoral stem prosthesis according to claim 14 wherein the proximal medial edge and/or the distal medial edge has a transverse cross-section that is semi-circular.

16. The femoral stem prosthesis according to claim 1 wherein the proximal lateral edge and/or the distal lateral edge has a transverse cross-section that is curved, rounded, oval, square, or trapezoidal.

17. The femoral stem prosthesis according to claim 16 wherein the proximal lateral edge and/or the distal lateral edge has a transverse cross-section that is generally flat or gently curved in an anterior-posterior direction.

18. The femoral stem prosthesis according to claim 1 wherein the distal lateral edge comprises a proximal to distal curve.

19. The femoral stem prosthesis according to claim 1 further comprising a neck configured for use with an offset sleeve or femoral head.

20. A femoral implant comprising the femoral stem prosthesis according to claim 1 and a femoral head prosthesis.

* * * * *